(12) United States Patent
Meech

(10) Patent No.: US 12,005,192 B2
(45) Date of Patent: Jun. 11, 2024

(54) CONNECTORS FOR RESPIRATORY ASSISTANCE SYSTEMS

(71) Applicant: Fisher & Paykel Healthcare Limited, Auckland (NZ)

(72) Inventor: Julio Derek Meech, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 290 days.

(21) Appl. No.: 16/625,541

(22) PCT Filed: Jun. 22, 2018

(86) PCT No.: PCT/NZ2018/050088
§ 371 (c)(1),
(2) Date: Dec. 20, 2019

(87) PCT Pub. No.: WO2018/236228
PCT Pub. Date: Dec. 27, 2018

(65) Prior Publication Data
US 2021/0138176 A1 May 13, 2021

Related U.S. Application Data

(60) Provisional application No. 62/523,998, filed on Jun. 23, 2017.

(51) Int. Cl.
*A61M 16/08* (2006.01)
*A61M 11/00* (2006.01)
(Continued)

(52) U.S. Cl.
CPC ........ *A61M 16/0833* (2014.02); *A61M 11/00* (2013.01); *A61M 15/009* (2013.01);
(Continued)

(58) Field of Classification Search
CPC ............ A61M 15/009; A61M 16/0833; A61M 16/0825
See application file for complete search history.

(56) References Cited

U.S. PATENT DOCUMENTS 3,612,048 A 10/1971 Takaoka
3,814,103 A * 6/1974 Fettel ................ A61M 16/0666
128/207.18
(Continued)

FOREIGN PATENT DOCUMENTS

AU 2009245802 B2 11/2013
AU 2015264908 A1 12/2015
(Continued)

OTHER PUBLICATIONS

International Preliminary Report on Patentability in corresponding International Patent Application No. PCT/NZ2018/050088, dated Dec. 24, 2019, in 10 pages.
(Continued)

*Primary Examiner* — Bradley H Philips
(74) *Attorney, Agent, or Firm* — Knobbe, Martens, Olson & Bear, LLP

(57) ABSTRACT

Connectors for respiratory assistance systems are disclosed. The connectors include an inspiratory conduit port, an expiratory conduit port, a first interface port, a second interface port, and a body or body portion formed between the inspiratory conduit port, the expiratory conduit port and the first and second interface ports, the body or body portion defining an interior cavity that fluidly couples, at least in part, the inspiratory conduit port and the expiratory conduit port to the first and second interface ports. The first and second interface ports are each fluidly couplable to a patient interface. Preferably, the first interface port is adapted to be coupled to an adult patient interface and the second interface
(Continued)

port is adapted to be coupled to a pediatric or neonatal patient interface.

16 Claims, 9 Drawing Sheets

(51) Int. Cl.
 *A61M 15/00* (2006.01)
 *A61M 16/00* (2006.01)
 *A61M 16/06* (2006.01)
 *A61M 16/16* (2006.01)
 *A61M 39/20* (2006.01)

(52) U.S. Cl.
 CPC .... *A61M 16/0057* (2013.01); *A61M 16/0666* (2013.01); *A61M 16/0825* (2014.02); *A61M 16/16* (2013.01); *A61M 39/20* (2013.01); *A61M 2240/00* (2013.01)

(56) References Cited

U.S. PATENT DOCUMENTS

| | | | |
|---|---|---|---|
| 3,903,884 | A | 9/1975 | Huston et al. |
| 4,020,834 | A | 5/1977 | Bird |
| 4,248,217 | A | 2/1981 | Brisson |
| 4,333,451 | A | 6/1982 | Paluch |
| 4,367,734 | A | 1/1983 | Benthin |
| 4,557,261 | A | 12/1985 | Rugheimer |
| 4,558,708 | A | 12/1985 | Labuda et al. |
| 4,580,556 | A * | 4/1986 | Kondur ............ A61M 16/0463 128/206.28 |
| 4,668,218 | A | 5/1987 | Virtanen |
| 4,723,543 | A | 2/1988 | Beran |
| 4,773,448 | A | 9/1988 | Francis |
| 4,787,655 | A | 11/1988 | Gross et al. |
| 4,817,822 | A | 4/1989 | Rand et al. |
| 4,819,629 | A | 4/1989 | Jonson |
| 4,827,921 | A | 5/1989 | Rugheimer |
| 5,036,840 | A | 8/1991 | Wallace |
| 5,062,420 | A * | 11/1991 | Levine ............ A61M 16/0816 128/207.14 |
| 5,099,833 | A | 3/1992 | Michaels |
| 5,178,138 | A | 1/1993 | Walstrom et al. |
| 5,195,980 | A | 3/1993 | Catlin |
| 5,228,436 | A | 7/1993 | Parkin |
| 5,297,543 | A | 3/1994 | Larson et al. |
| D362,503 | S | 9/1995 | Cook et al. |
| 5,460,172 | A | 10/1995 | Eckerbom et al. |
| 5,474,058 | A * | 12/1995 | Lix ............ A61M 16/0833 128/200.14 |
| 5,546,930 | A | 8/1996 | Wikefeldt |
| 5,720,282 | A * | 2/1998 | Wright ............ A61M 16/04 128/207.14 |
| 5,735,271 | A * | 4/1998 | Lorenzen ............ A61M 16/0833 128/207.14 |
| 5,776,117 | A | 7/1998 | Haselhorst et al. |
| 5,988,164 | A | 11/1999 | Paluch |
| 6,102,038 | A | 8/2000 | DeVries |
| 6,209,539 | B1 | 4/2001 | Loescher et al. |
| D492,030 | S | 6/2004 | Rani |
| D492,773 | S | 7/2004 | Elllingboe et al. |
| D519,632 | S | 4/2006 | Bayron et al. |
| 7,152,597 | B2 | 12/2006 | Bathe |
| 7,162,921 | B2 | 1/2007 | Gerder et al. |
| D547,447 | S | 7/2007 | Bruce et al. |
| 7,634,998 | B1 | 12/2009 | Fenley |
| 7,841,341 | B2 | 11/2010 | Dhuper et al. |
| 7,926,484 | B2 | 4/2011 | Dhuper et al. |
| D649,240 | S | 11/2011 | Lewis et al. |
| 8,151,794 | B2 | 4/2012 | Meyer et al. |
| D672,459 | S | 12/2012 | Miller |
| D685,906 | S | 7/2013 | Dale et al. |
| D689,187 | S | 9/2013 | Kruger |
| D691,717 | S | 10/2013 | McLean et al. |
| 8,720,435 | B2 | 5/2014 | Gallem et al. |
| 8,746,241 | B2 * | 6/2014 | Cavendish ........ A61M 16/0816 128/203.12 |
| D709,612 | S | 7/2014 | Lewis |
| D723,681 | S | 3/2015 | Ingram et al. |
| D747,473 | S | 1/2016 | Martin et al. |
| 9,539,401 | B2 | 1/2017 | Tatkov |
| 10,143,818 | B2 | 12/2018 | Martin et al. |
| 10,369,313 | B2 | 8/2019 | White et al. |
| 10,532,173 | B2 | 1/2020 | Tatkov |
| 11,351,325 | B2 | 6/2022 | Martin et al. |
| 11,439,786 | B2 | 9/2022 | Tatkov |
| 2003/0116167 | A1 | 6/2003 | Hooser |
| 2004/0016302 | A1 | 1/2004 | Misholi et al. |
| 2004/0089296 | A1 * | 5/2004 | Bowden ............ A61M 16/08 128/203.12 |
| 2004/0168690 | A1 * | 9/2004 | Payne ............ B65D 47/0838 128/207.14 |
| 2005/0188990 | A1 | 9/2005 | Fukunaga et al. |
| 2005/0229928 | A1 | 10/2005 | Irvi et al. |
| 2006/0173420 | A1 | 8/2006 | Fangrow, Jr. |
| 2006/0283447 | A1 | 12/2006 | Dhuper et al. |
| 2007/0083677 | A1 | 4/2007 | Cecka et al. |
| 2007/0101994 | A1 | 5/2007 | Waters |
| 2007/0193581 | A1 | 8/2007 | Laurila et al. |
| 2008/0077063 | A1 | 3/2008 | Meyer et al. |
| 2008/0264412 | A1 | 10/2008 | Meyer et al. |
| 2008/0264418 | A1 | 10/2008 | Schermeier et al. |
| 2009/0105692 | A1 | 4/2009 | Lopez et al. |
| 2009/0124983 | A1 | 5/2009 | Ferrari |
| 2009/0301476 | A1 | 12/2009 | Korneff et al. |
| 2010/0071688 | A1 | 3/2010 | Dwyer |
| 2010/0071695 | A1 | 3/2010 | Thiessen |
| 2010/0139653 | A1 | 6/2010 | Schloss |
| 2010/0163022 | A1 * | 7/2010 | Brewer ............ A61M 16/0463 128/200.24 |
| 2010/0163051 | A1 | 7/2010 | Brewer et al. |
| 2010/0242622 | A1 | 9/2010 | Weckstrom |
| 2011/0088696 | A1 | 4/2011 | Ratner |
| 2011/0146670 | A1 | 6/2011 | Gallem et al. |
| 2011/0284007 | A1 | 11/2011 | Pierre |
| 2012/0180791 | A1 | 7/2012 | Ciccone et al. |
| 2012/0255545 | A1 | 10/2012 | Meyer et al. |
| 2013/0081616 | A1 | 4/2013 | Tatkov |
| 2013/0146053 | A1 | 6/2013 | Mazela et al. |
| 2013/0269686 | A1 | 10/2013 | Pezzano et al. |
| 2014/0166011 | A1 | 6/2014 | Peirro et al. |
| 2014/0276178 | A1 | 9/2014 | Simon |
| 2015/0021909 | A1 | 1/2015 | Gulliver et al. |
| 2015/0314093 | A1 | 11/2015 | Chiu |
| 2016/0038700 | A1 | 2/2016 | White et al. |
| 2017/0007797 | A1 * | 1/2017 | Islava ............ A61M 16/0825 |
| 2017/0100558 | A1 | 4/2017 | Dhuper et al. |
| 2017/0246417 | A1 | 8/2017 | Kemps et al. |
| 2018/0272084 | A1 * | 9/2018 | Reiner ............ A61M 15/0065 |
| 2019/0111229 | A1 | 4/2019 | Martin et al. |
| 2020/0289780 | A1 | 9/2020 | Kemps et al. |
| 2022/0339388 | A1 | 10/2022 | Martin et al. |
| 2022/0409842 | A1 | 12/2022 | Tatkov |

FOREIGN PATENT DOCUMENTS

| | | |
|---|---|---|
| CN | 201912587 U | 8/2011 |
| DE | 3703441 A1 | 8/1988 |
| DE | 102007009449 B3 | 1/2008 |
| DE | 202011107902 U1 | 1/2012 |
| EP | 0604399 A1 | 6/1994 |
| EP | 1820528 A1 | 8/2007 |
| EP | 2044921 B1 | 7/2011 |
| FR | 2725627 A1 | 4/1996 |
| GB | 750672 A | 6/1956 |
| GB | 1290484 A | 9/1972 |
| GB | 1317315 A | 5/1973 |
| GB | 2412877 A | 10/2005 |
| JP | 2004-033550 A | 2/2004 |
| WO | WO 1999/059517 A1 | 11/1999 |
| WO | WO 2003/041780 A2 | 5/2003 |

(56) References Cited

FOREIGN PATENT DOCUMENTS

| WO | WO 2005/048982 | 6/2005 | |
|----|----|----|----|
| WO | WO-2005048982 A2 * | 6/2005 | ......... A61K 31/7036 |
| WO | WO 2012/030232 A1 | 3/2012 | |
| WO | WO 2013/147623 A1 | 10/2013 | |
| WO | WO 2013/162386 A1 | 10/2013 | |
| WO | WO 2014/116122 A1 | 7/2014 | |
| WO | WO 2015/174859 A2 | 11/2015 | |
| WO | WO 2017/037660 A1 | 3/2017 | |

OTHER PUBLICATIONS

International Search Report, PCT/NZ2018/050088, dated Sep. 17, 2018; 5 pages.

\* cited by examiner

CONNECTORS FOR RESPIRATORY ASSISTANCE SYSTEMS

BACKGROUND

Technical Field

The present disclosure generally relates to respiratory assistance systems. More particularly, the present disclosure relates to connectors for respiratory assistance systems.

Description of the Related Art

A respiratory assistance system may be used to provide respiratory gases to a patient from a gases source via an inspiratory conduit in fluid communication between the gases source and a patient interface. Examples of a patient interface may include an oral mask, a nasal mask, a nasal cannula, a tracheal mask, an endotracheal tube, or combinations thereof. In a respiratory assistance system where the gases source is a ventilator, gases exhaled by the patient into the patient interface may be returned via an expiratory conduit in fluid communication between the patient interface and the ventilator. Other arrangements are also possible. The inspiratory conduit and the expiratory conduit may be connected to the patient interface via a wye-piece.

While wye-pieces may be connected directly to a patient interface, to provide for improved patient comfort, wye-pieces may alternatively be connected to patient interfaces via a short, lightweight, flexible tube or tubes. Thus wye-pieces have at least 3 ports, one for coupling to an inspiratory conduit, one for coupling to an expiratory conduit or vent and one for couplings or connections to the patient interface. As will be appreciated, these may be direct or indirect couplings and reference to patient interface port or the like throughout the specification is not to be interpreted in a limited way to require a physical connection between the wye-piece and the other component in question, rather, only that they be at least fluidly coupled. Further ports may also be provided. For example, these may be provided for injecting aerosols or other medications or substances into the gases flow, particularly the inspiratory flow, or they may be provided for a gases monitoring device (such as a device for measuring a property of gases flowing through the connector, including, by way of non-limiting example, humidity, temperature, flow, and/or pressure) in the inspiratory or expiratory flow or in any portion of the connector.

A respiratory assistance system may include a humidification device to condition respiratory gases provided to the patient. The humidification device may include a humidification chamber containing liquid and a heater adjacent the humidification chamber to heat the liquid to produce vapor. The humidification device may be positioned in the fluid communication path between the gases source and the patient interface to heat and/or humidify respiratory gases prior to delivery via the inspiratory conduit to the patient interface. Respiratory gases delivered to a patient at 100% relative humidity and 37° C. mimic the properties resulting from the transformation of air that occurs as it passes through the patient's nose to the lungs. This promotes efficient gas exchange and ventilation in the lungs, aids defense mechanisms in the airway, and increases patient comfort during treatment.

Conventional wye-pieces are generally Y-shaped with the inspiratory and expiratory tubes being connectable via respective adjacent ports at a first end of the wye-piece and a patient interface being connectable via a port at the opposite end of the wye-piece such that flow through each of the ports is substantially parallel, although the inspiratory and expiratory ports often diverge to some degree moving away from the patient interface port. While generally suitable for many patients, this arrangement is not without problems. The wye-piece and connectors of the conduits and patient interface are typically formed from substantially rigid plastics. Together these form a rigid component having a certain length which can restrict positioning or movement in some environments and/or cause patient discomfort. For example, this can be a particular problem for neo-natal patients positioned within an incubator. Further this single configuration does nothing to address individual preferences on arrangement of the breathing circuit components.

A further important consideration is that wye pieces tend to create dead space within the circuit i.e. portions of the circuit that are not heated and so prone to cause cooling of gases therethrough, which in turn will tend to promote undesired condensation build up. Moreover, these lengthen the path between the patient interface and the expiratory limb, thereby increasing the likelihood and/or amount of gas that may be rebreathed.

It is an object of the invention to address or at least ameliorate at least one of the aforementioned problems. Alternatively, it is an object to at least provide a useful alternative to prior art arrangements.

SUMMARY

Thus, in broad terms, the invention provides a connector, preferably generally in the form of a wye-piece, having first and second ports for directly or indirectly connecting, or fluidly coupling, to an inspiratory conduit and an expiratory conduit, respectively, and at least two additional ports for directly or indirectly connecting to a patient interface, wherein the additional ports have different orientations relative to the first and second ports, such that, depending on which of the at least two additional ports that a patient interface is connected to, the orientation of the patient interface relative to the inspiratory tube and expiratory tube is altered. The one or more additional ports not connected to the patient interface may be selectively closable, for example, using a stopper or bung, or other form of closure.

According to a first aspect, there is provided a connector for a respiratory assistance system comprising an inspiratory conduit port, an expiratory conduit port, a first interface port, a second interface port, and a body or body portion formed between the inspiratory conduit port, the expiratory conduit port and the first and second interface ports, the body or body portion defining an interior cavity that fluidly couples, at least in part, the inspiratory conduit port and the expiratory conduit port to the first and second interface ports, wherein the first and second interface ports are each fluidly couplable to a patient interface.

The inspiratory conduit port, the expiratory conduit port and the first interface port may be aligned or substantially aligned. Alternatively, where the inspiratory conduit port and the expiratory conduit port are provided at ends of respective branches that diverge moving away from the first interface port, the first interface port may lie in a plane bisecting axes through the inspiratory conduit port and the expiratory conduit port.

The second interface port is preferably angularly offset relative to the inspiratory conduit port and/or the expiratory conduit port and/or the first second interface port by between 45° and 135°, preferably between 60° and 120°, and more preferably by or by about 90°.

The inspiratory conduit port and the expiratory conduit port may be rotatably coupled to the body or body portion about a first axis. In some configurations, the inspiratory conduit port and the expiratory conduit port may be arranged to be freely rotatable in relation to the body or body portion about the first axis by means of a rotatable connection, e.g. swivel connection. Alternatively, a mechanical stop may limit the amount of rotation about the first axis, to, for example, 90°, or 180°, or 270°, or 360° (i.e. one full rotation). The first axis may extend through the center or approximate center of the first interface port, "center" being with reference to a section though the first interface port in a plane substantially perpendicular to a general flow of gases though the port, in use.

The inspiratory conduit port and/or the expiratory conduit port may be integrally formed. Further, the inspiratory conduit port and/or the expiratory conduit port may be integrally formed with the body or body portion. Additionally or alternatively, the first interface port may be integrally formed with the body or body portion and/or the second interface port may be integrally formed with the body or body portion.

The connector may include an inspiratory branch including the inspiratory conduit port, the inspiratory branch extending from or formed by the body or body portion. Additionally or alternatively, the connector may include an expiratory branch including the expiratory conduit port, the expiratory branch extending from or formed by the body or body portion. Additionally or alternatively, the connector may include a first interface branch including the first interface port, the first interface branch extending from or formed by the body or body portion. Additionally or alternatively, the connector may include a second interface branch including the first interface port, the second interface branch extending from or formed by the body or body portion. According to such embodiments, the inspiratory conduit port may be located at a conduit end of the inspiratory branch, and/or the expiratory conduit port may be located at a conduit end of the expiratory branch, and/or the first interface port may be located at a patient interface end of the first interface branch, and/or the second interface port may be located at a patient interface end of the second interface branch. Further, the conduit end of the inspiratory branch is preferably adapted to be connected to an inspiratory conduit, and/or the conduit end of the expiratory branch is preferably adapted to be connected to an expiratory conduit, and/or the patient interface end of the first interface branch and/or the patient end of the second interface branch is preferably adapted to be connected to a patient interface.

The first interface port and/or the second interface port may be selectively closable. By way of non-limiting example, the first interface port and/or the second interface port may be adapted to sealingly engage a stopper, the stopper being configured to be removably received in and/or about the first interface port and/or the second interface port to selectively close the respective port. The stopper may include a hook or loop extending therefrom, enabling the connector, and respiratory circuit components attached thereto, to be hung on a medical stand when not in use. The hook or loop may additionally or alternatively aid a user in removing the stopper from a port. The hook or loop may additionally or alternatively removably or irremovably attach the stopper to the connector to prevent it from becoming separated from the connector and lost. Other forms of closure for selectively closing a port may alternatively be used.

Selectively closing at least one of the ports, e.g. one of the expiratory ports, by means of a closure may be advantageous in therapies where e.g. the expiratory limb is not connected to the connector.

Similar to the first interface port and/or the second interface port, the expiratory port may also be selectively closeable. The option of selectively closing the expiratory port makes the connector more versatile, as the same connector e.g. could be used when transitioning from one therapy to another, e.g. when going from a ventilator-based invasive therapy to a high flow nasal therapy. For example, in high flow nasal therapies where a nasal cannula is non-sealingly arranged to the nares of the patient, the expiratory port could be selectively closed, as high flow nasal therapies are generally open systems in which patient's expiratory gases may escape via the space between the cannula prongs and the nares, and hence there is no need for connecting an expiratory limb to the expiratory port.

Also, in some cases, it may be possible to re-use the same connector and optionally at least one conduit connected thereto, when transitioning from one therapy to the other, thereby making the transitioning more user friendly and/or quicker and/or more cost effective. For instance, in an example where a patient is being changed from invasive therapy via an endotracheal tube to high flow therapy via an unsealed nasal cannula, this may be accomplished with minimal user steps by changing the connection at the patient interface port from the endotracheal tube interface to the nasal cannula interface, removing and discarding the expiratory limb of the breathing circuit, and closing, blocking, or stoppering the expiratory port of the wye piece (as the open system of high flow therapy does not generally require an expiratory limb). In this way, the patient or carer may avoid the expense and/or inconvenience of opening and setting up the components of an additional circuit kit to transition therapies.

Accordingly, the same connector may be used and adapted for different therapeutic purposes. As such it may be left in place for convenience. Alternatively, or additionally, at least some of the ports of the connector, when not required for the active therapy, may be connected to pressure sensing and/or medicament delivery unit(s). At least the size of the device for closure may change depending on the port to which it connects. Other changes may be made such as provision of a port for sensing, etc. in the device for closure.

The stopper may comprise a port for coupling to a gases treatment device and/or a gases monitoring device.

At least a portion of the connector may be opaque and/or transparent.

At least one of the interface ports may be adapted to be coupled to a gases treatment device and/or a gases monitoring device.

The connector may include at least one additional port. At least one of said additional port(s) may be adapted to be coupled to a gases treatment device and/or a gases monitoring device.

The first interface port may be adapted to be coupled to an adult interface and the second interface port may be adapted to be coupled to a pediatric interface or a neonatal interface. Thus, for adult patients or older, larger pediatric patients (such as children in primary (elementary) school, intermediate (middle) school, or teenagers), the connector may have a conventional wye-piece-type configuration but an alternative configuration for younger pediatric or neonatal patients, where the patient interface port has a different orientation. According to preferred embodiments, the orientation of the patient interface port is offset by about 90° for younger pediatric patients relative to the configuration for adult or nearer-adult patients. Such an orientation can provide for greater comfort and usability, particularly where there are space constraints to the sides of a patient. It should be appreciated that the ports, e.g. interface ports, of the connector may be interchangeable. As such one interface port need not be solely designated for larger pediatric patients and another interface port solely designated for smaller patients. Due to space constraints and other situational medical considerations it may well be that one interface port is more preferred than another for connection to larger pediatric patients rather than smaller patients. However, from a technical perspective each of the interface ports are equally capable of connection to any patient interface regardless of the size of the patient. That said, as required, an adaptor may be required in some instances to facilitate connections between component connectors of different types, e.g. an adaptor may be in the form of a short conduit having first and second ends, the first end connecting to a port of the connector and the second end connecting to the component to be connected to the port. At the simplest level, the first and second ends may have different diameters or medical tapers.

While the different interface ports are particularly described as being adapted for connecting to adult or older pediatric patients and younger pediatric or neonatal patients, respectively, the invention is not limited thereto. For example, the same patient or type of patient may use the connector of the present invention in multiple, different ways depending on personal preferences. Moreover, patients may vary the configuration depending on how the device is being used. For example, one configuration may be used while a patient is seated and another one while the patient is lying down. Environmental factors may also play a part in which set up is selected. For example, obstructions in the patient's room or bedspace may constrain where components of the system may be positioned and/or there may be natural placement points such as tables, poles, sheets, bed frames, etc. that provide positions (whether fixed or movable) onto which component parts of the system may be conveniently positioned.

So, according to preferred embodiments, the connector is configurable in at least two configurations, wherein in a first configuration the first interface port is coupled to an adult or near-adult interface and in a second configuration the second interface port is coupled to a pediatric and/or neonatal interface. In the first configuration, a gases treatment device and/or a gases monitoring device may be coupled to the second interface port. In the second configuration, a gases treatment device and/or a gases monitoring device may be coupled to the first interface port.

The gases treatment device may include a metered-dose inhaler or any other device that can be used to vary one or more properties of the gas, including through addition of substances and/or gases to gases flowing through the connector. For example, connection may be made to a supplemental oxygen supply. In another example, connection may be made to a nebulizer or a source of aerosolized medication.

The gases monitoring device may include any device for measuring a property of gases flowing through the connector, including, by way of non-limiting example, any one or more of humidity, temperature, flow and pressure. Such monitoring devices may extend into the inner volume of the connector such that they are positioned inside the gases flow. Such monitoring devices may include sensors as are known in the art.

In an alternative realisation, rather than having plural potential interface connecting ports, a single interface port may be provided but the orientation of the single interface port relative to the inspiratory conduit port and the expiratory conduit port may be selectively altered such as by swivelling the interface port relative to the inspiratory and expiratory ports, preferably about an axis substantially perpendicular to an axis aligned with the interface port.

A single interface port provided connector for a respiratory assistance system may comprise an inspiratory conduit port, an expiratory conduit port, and the single interface port. A body or body portion may be formed between the inspiratory conduit port, the expiratory conduit port and the single interface port, the body or body portion defining an interior cavity that fluidly couples, at least in part, the inspiratory conduit port and the expiratory conduit port to the single interface port. The single interface port is fluidly couplable to a patient interface. The single interface port is rotatably operatively coupled in relation to the inspiratory conduit port and the expiratory conduit around an axis extending at an angle in relation to a longitudinal axis of either the inspiratory conduit port or expiratory conduit port, or a shared longitudinal axis of the inspiratory conduit port and expiratory conduit port. The single interface port may be rotatably operatively coupled by means of a swivel connection connecting the single interface port to the body. The angle between the axis around which the single interface port is rotatable and the longitudinal axis of either the inspiratory conduit port or expiratory conduit port, or the shared longitudinal axis, is substantially perpendicular. Alternatively, a ball-type joint may be used.

FIGS. 15 to 17 show different configurations of a connector having a single interface port.

In FIG. 15 the single interface port is connected to the ports 201 and 202 by means of a swivel connection. As may be observed the longitudinal axis of the single interface port 203 is essentially parallel to that (see dashed line of FIG. 15) of the main body 205 of the connector. By means of the swivel connection it is possible to reduce any rotational forces acting upon the connector, such as forces originating from the conduit connected thereto, in use. The swivel connection allows the single interface port 203 to rotate about the longitudinal axis of the main body 205, as indicated by the directional arrow in FIG. 15.

Turning to FIG. 16, the single interface port 203 is arranged at an angle α in relation to the longitudinal axis of the main body 205. Hence, the longitudinal axis of the interface port 203 is non-parallel to the longitudinal axis (see dashed line in FIG. 16) of the main body 205. A swivel connection, similar to that of FIG. 15 connects the main body 205 with the ports 201 and 202. It should be appreciated that the single interface port could be arranged at essentially any angle α in relation to the longitudinal axis of the main body. In preferred embodiments, the longitudinal axis of the single interface port may be arranged at an angle α in the range of 0° to 90° in relation to the longitudinal axis of the main body, e.g. at 45°. The swivel connection allows the single interface port 203 being offset to the longitudinal axis of the main body 205 by angle α to rotate about the longitudinal axis of the main body 205, as indicated by the directional arrow in FIG. 16.

FIG. 17 shows an alternative single interface port provided connector, wherein a ball joint 410 connects the single interface port 203 to the ports 201 and 202. The ball joint allows the single interface port 203 to attain a wide range of directional orientations in relation to the ports 201 and 202. The ball joint 410 may allow the single interface port to rotate about its own longitudinal axis, optionally in conjunction with attaining a range of angular orientations tilted at an angle in relation to the longitudinal axis of the main body, as indicated by the directional arrows in FIG. 17.

Preferably, the orientation of the interface port is alterable between at least two configurations in relation to the inspiratory and expiratory ports. A first configuration may be essentially the same as the aforementioned configuration for adult patients wherein the connector has a substantially conventional wye-piece configuration in terms of the configuration of the inspiratory port, expiratory port and interface port(s). A second configuration may be essentially the same as the aforementioned pediatric or neonatal configuration.

Preferably, the connector is configured to be releasably locked in at least the first and/or second orientation. It will be appreciated that similar adaptation could be made to the connector having two interface ports to provide further improvement in flexibility/comfort but at the expense of a greater number of component ports.

While preferred embodiments are adapted for use within a respiratory assistance system, the invention may be used within other systems. For example, it is known to be beneficial to use humidified gases in surgical procedures, such as insufflation procedures, and the connector of the present invention may be readily used within such systems.

Other features of the alternative realisation may be drawn from the description of the first aspect.

According to an aspect a connector for a respiratory assistance system is provided. The connector comprises four ports for conveying respiratory gases. Preferably, one or more or all of the ports are selectively closeable such that the connector can be used in different respiratory assistance system configurations. Other features of this aspect of the connector may be drawn from other embodiments of the invention.

BRIEF DESCRIPTION OF THE DRAWINGS

These and other aspects of the present disclosure will be described with reference to the following drawings, which should be considered illustrative but not limiting.

DETAILED DESCRIPTION

Figure 1:
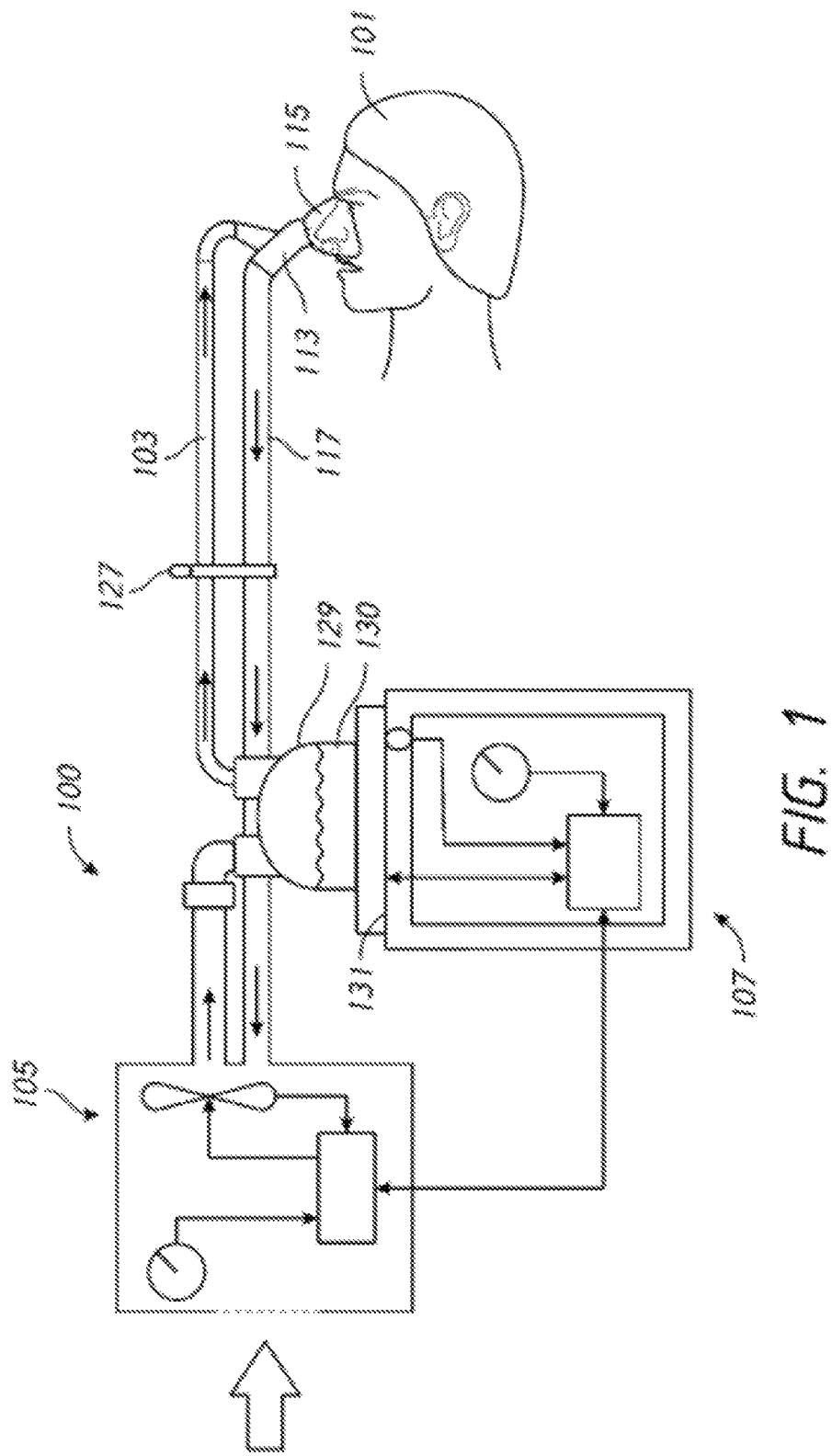
FIG. 1 is a diagram of an example respiratory assistance system that may be used to provide respiratory gases to a patient.

FIG. 1 is a diagram of an example respiratory assistance system 100 that may be used to provide respiratory gases to a patient 101. The respiratory assistance system 100 comprises a gases source 105 in fluid communication with a patient interface 115 via an inspiratory conduit 103 and an expiratory conduit 117. In some configurations, the gases source 105 comprises a ventilator. The inspiratory conduit 103 and the expiratory conduit 117 are connected to the patient interface 115 via a wye-piece 113.

In the configuration shown, the respiratory assistance system 100 also comprises a humidification device 107 to condition respiratory gases provided to the patient 101. The humidification device 107 is positioned in the fluid communication path between the gases source 105 and the patient interface 115 to heat and/or humidify respiratory gases prior to delivery via the inspiratory conduit 103 to the patient interface 115. The humidification device 107 comprises a humidification chamber 129 containing a liquid 130 and a heater 131 adjacent to the humidification chamber 129 to heat the liquid 130 to produce vapor that humidifies respiratory gases passing over the liquid 130. In some configurations, the gases source 105 and the humidification device 107 are located within a common housing and/or comprise components of a single apparatus. In some configurations, the gases source 105 is connected directly to the patient interface 115 via the inspiratory conduit 103 with no intervening humidification device.

In some configurations, the inspiratory conduit 103 includes a heating component, such as a heater wire, to keep heated and humidified respiratory gases delivered via the inspiratory conduit 103 to the patient interface 115 warm and to reduce formation of condensate in the inspiratory conduit 103. In some configurations, the wye-piece 113 and/or the patient interface 115 might include a similar heating feature, so vapor present in heated and humidified respiratory gases delivered via the inspiratory conduit 103 to the wye-piece 113 do not condense in the wye-piece 113 and/or the patient interface 115.

Figure 2:
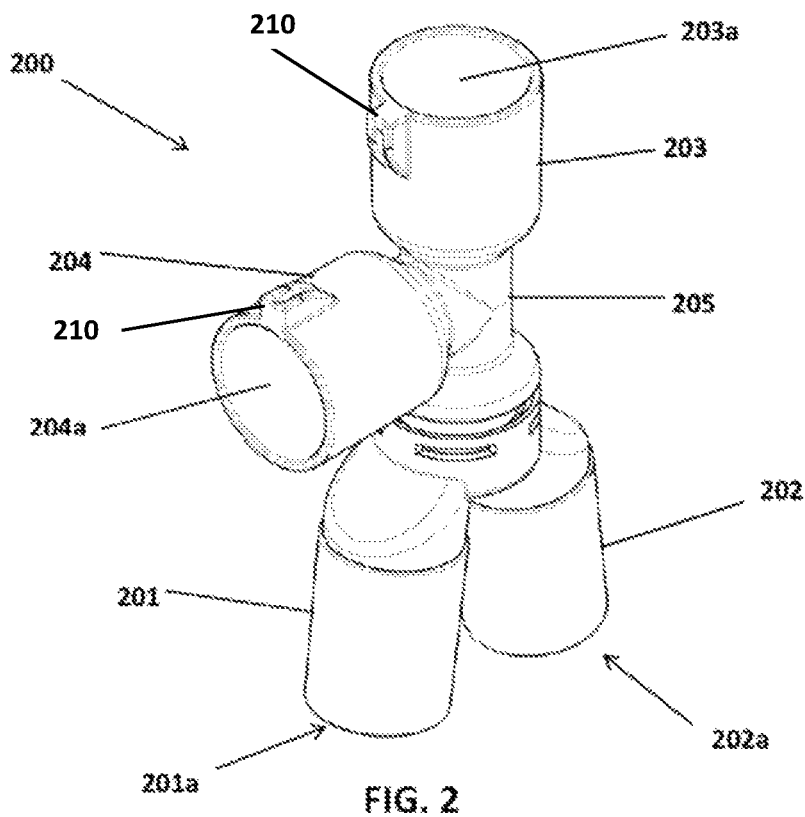
FIGS. 2 to 4 provide perspective, side and sectional views, respectively, of a connector for a respiratory assistance system according to an example embodiment.
Figure 3:
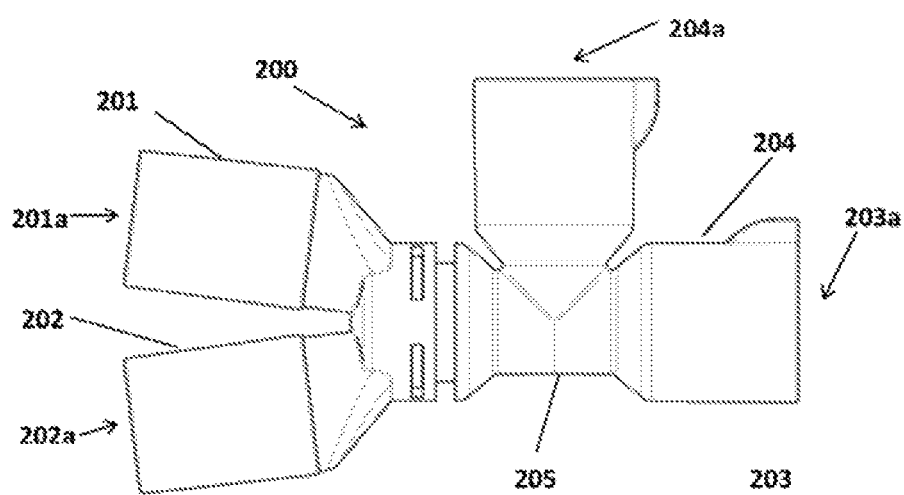
Figure 4:
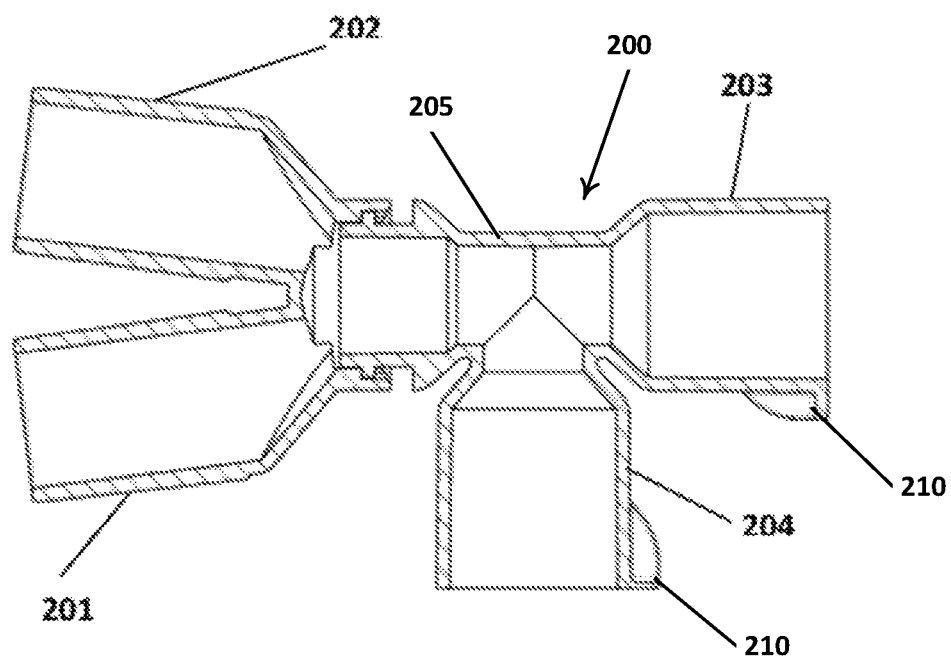

FIGS. 2 to 4 provide perspective, side and sectional views, respectively, of a connector 200 according to an embodiment of the invention. The connector 200 of this embodiment is generally in the form of a wye-piece but includes an additional interface port. Both interface ports are capable of and suitable for passing the whole bulk inspiratory and expiratory flow of the patient, as well as any bias bulk flow of gases provided by the gases source in excess of the patient's inspiratory demand. More particularly, the connector 200 includes an inspiratory branch 201, an expiratory branch 202 and two interface branches 203, 204, all extending from the main body or main body portion 205 of the connector 200. At the end of each branch distal from the main body 205, there is provided a respective port 201a, 202a, 203a, 204a. Although referred to above as inspiratory, expiratory and interface branches, each of the branches are in fact interchangeable. Accordingly, branch 201 could alternatively be used also as an expiratory or interface branch. Branch 202 could alternatively be used also as an inspiratory or interface branch. Branches 203, 204 could alternatively be used as inspiratory and expiratory branches, respectively. This branch interchangeability provides the connector with improved versatility.

While branches 201, 202 and ports 201a, 202a in some embodiments are designated as being for connecting to an inspiratory conduit and an expiratory conduit, respectively, according to other embodiments, the inspiratory and expiratory branches may be substantially identical so that both conduits can connect to either branch 201, 202 or port 201a, 202a. Other connections are also possible. For example, one of said ports 201a, 202a may be open to, or at least in fluid communication with, the atmosphere. Additionally or alternatively, a vent or valve or ventilator-controlled (i.e. pressure-controlled) valve may be provided to selectively and/or partially open and/or close one or both of the ports 201*a*, 202*a*. Thus, for example, provision may be made for all or a portion of the expiratory gases from a patient to be vented to atmosphere. Additionally or alternatively, an Anti-Asphyxiation or AA-valve may be incorporated in or otherwise associated with the inspiratory branch so as to allow a patient to inhale atmospheric gases in the event that the supply of gases from the gases source 105 is interrupted.

The main body 205 and branches 201-204 define internal passageways that provide a fluid connection between the insides of the branches 201-204 and the inside of the main body 205, as best seen in FIG. 4. Thus, in use, inspiratory gases may be received into the main body 205 via inspiratory port 201*a* and conveyed to a patient interface via inspiratory branch 201, main body 205 and either interface branch 203 and interface port 203*a* or interface branch 204 and interface port 204*a*. Conversely, expiratory gases may be received at interface port 203*a* or 204*a*, conveyed along the corresponding expiratory branch 203, 204 to the main body 205, and out through the expiratory port 202*a* via the expiratory branch 202. As will be appreciated, this description of flow is a description of the general intended flow of the bulk of gases through the connector 200 and is non-limiting. For example, some inspiratory gases may pass to the expiratory port without passing through an interface port. Similarly, some expiratory gases may be breathed in again by a patient.

Additionally, the main body 205 and/or at least one of the branches may be provided with at least one auxiliary port. The at least one auxiliary port may e.g. be used for sensing a parameter of interest, e.g. pressure, humidity, temperature, flow rate. Alternatively, or additionally the at least one auxiliary port may be used in association with medication delivery. Alternatively, or additionally the at least one auxiliary port could be used for suctioning patient secretions, inspections or monitoring e.g. using a bronchoscope. Other uses and/or configurations of auxiliary port(s) will be apparent to those skilled in the art and are included within the scope of the invention.

According to preferred embodiments, the connector is configured to be of generally reduced size as compared to more conventional wye piece connectors. More particularly, the main body is very much reduced in size, particularly length. The same is preferably true of the branches joined to the main body. Reducing the size of the connector and/or the length of the flow path therethrough reduces dead space and condensation forming as a result thereof. The reduced size and/or length of the connector in turn reduces the interior volume of the connector. Since the interior volume in some configurations is a shared inspiratory/expiratory pathway, with reduced interior volume for the connector, the distance exhaled gases must travel to exit through the expiratory port 202*a* (away from the interface port) is reduced, thereby reducing the amount of exhaled gas that may be re-breathed in.

To connect to inspiratory and expiratory conduits, the ports 201*a*, 202*a* are configured to be operatively, e.g. sealingly or substantially sealingly, coupled to an end of an inspiratory conduit and an expiratory conduit, respectively. As will be understood by those skilled in the art, to this end, a connector may be provided at the ends of the inspiratory and expiratory conduits to facilitate such connection. For example, the inside and/or outside of the connectors at the ends of the conduits may be tapered and configured to receive therein or thereabout a respective end of branches 201, 202, providing a frictional engagement between the conduit connectors and the respective branch 201, 202. Seals may optionally be provided. For example, an O-ring may be positioned between the engaging surfaces of the conduits connectors and the respective end of branches 201, 202. Alternative forms of connection are also within the scope of the invention. For example, snap fit-type connections and/or sprung clip or button type connections that require actuation to enable separation of the connected components are also envisaged. According to some alternative embodiments the inspiratory conduit and/or expiratory conduit and/or respective connectors at the ends thereof may be fixedly attached to or at least in part integral with the branches 201, 202, respectively.

Interface branches 203, 204 may be used to connect to a patient interface, including via intermediate conduits and/or connectors. While branches 203, 204 are shown as being substantially identical, albeit with different orientations, the invention is not limited thereto. For example, the interface ports 203*a*, 204*a* may have different sizes so as to connect to different types of interface.

In the embodiment shown in FIGS. 2 to 4, the inspiratory and expiratory branches 201, 202 are formed integrally and rotatably attached to the main body 205. Referring in particular to FIG. 4, the integrally formed inspiratory and expiratory branches may be configured to snap-fit into engagement with the main body 205 with a sufficient tolerance in the fit that friction between the component parts does not hinder rotation. A suitable seal (such as an o-ring or other sealing apparatus as is known in the art) may be provided to prevent leakage of gases. The ability to swivel the inspiratory and expiratory branches 201, 202 can provide for greater ease of setup and further provide for improved patient comfort. According to the embodiment shown, the axis of rotation lies in a plane bisecting the inspiratory and expiratory branches 201, 202 although the invention is not limited thereto. Alternatively, the inspiratory and/or expiratory branches 201, 202 may be formed integrally with the main body 205. Regardless of whether the inspiratory and expiratory branches 201, 202 are rotatable as a unit, one or both may provide for independent rotation about its own axis for the respective inspiratory conduit and expiratory conduit when connected thereto.

Figure 5:
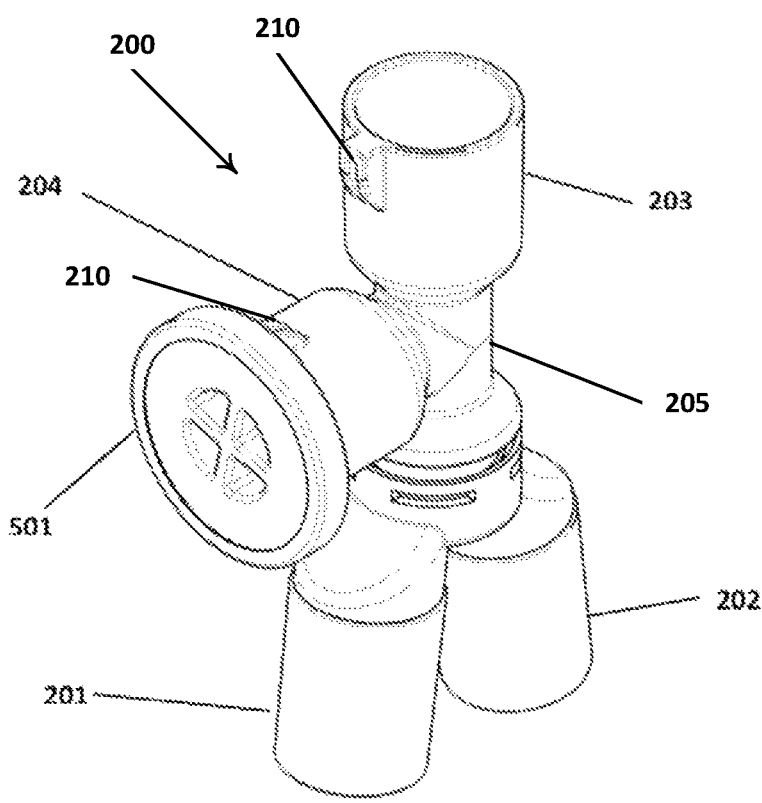
FIGS. 5 to 6 provide perspective and sectional views, respectively, of the connector of FIGS. 2-4 with a stopper coupled to an interface port thereof.
Figure 6:
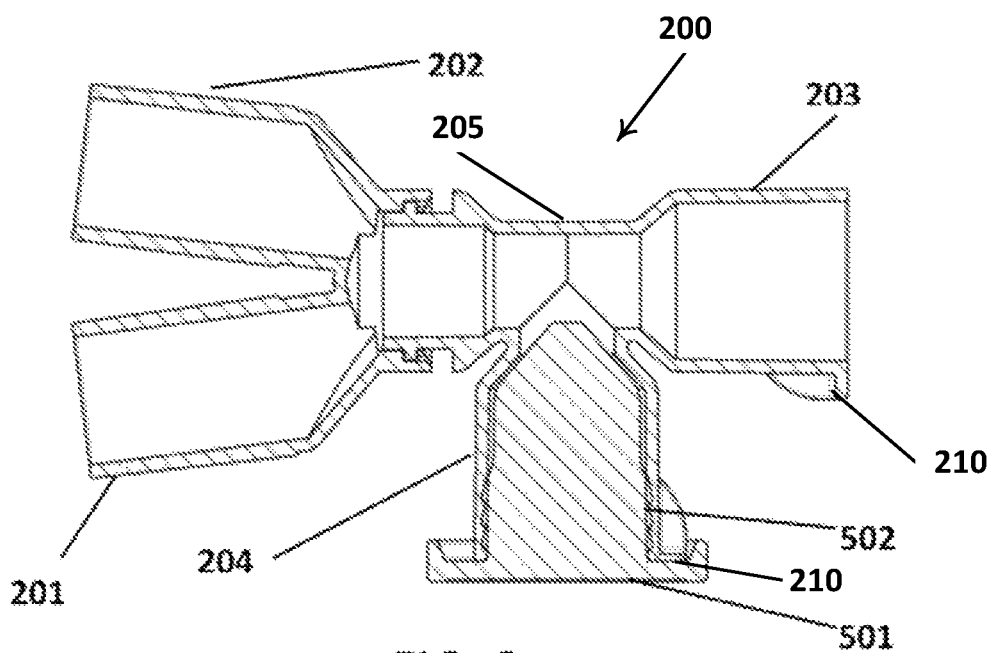
Figure 7:
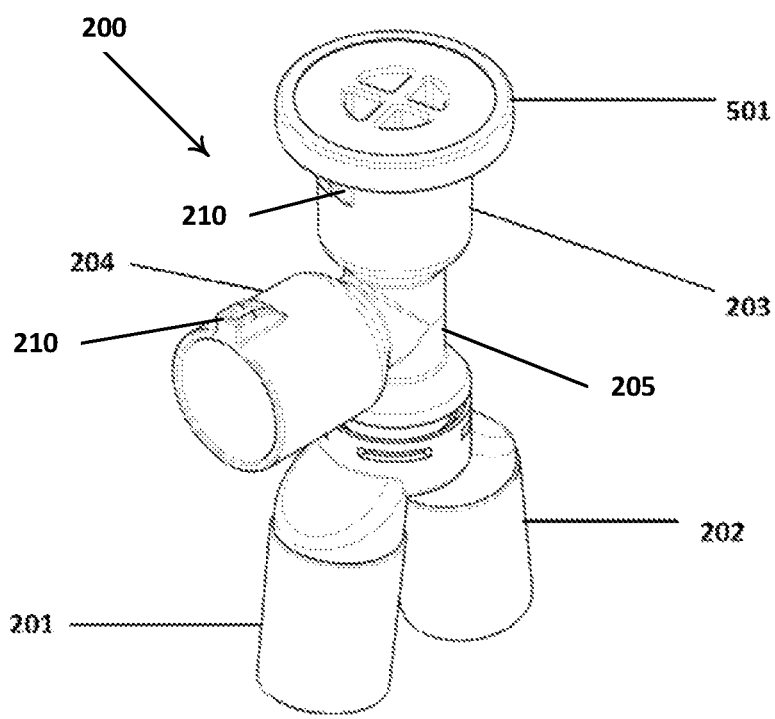
FIGS. 7 to 8 provide perspective and sectional views, respectively, of the connector of FIGS. 2-4 with a stopper coupled to another interface port thereof.
Figure 8:
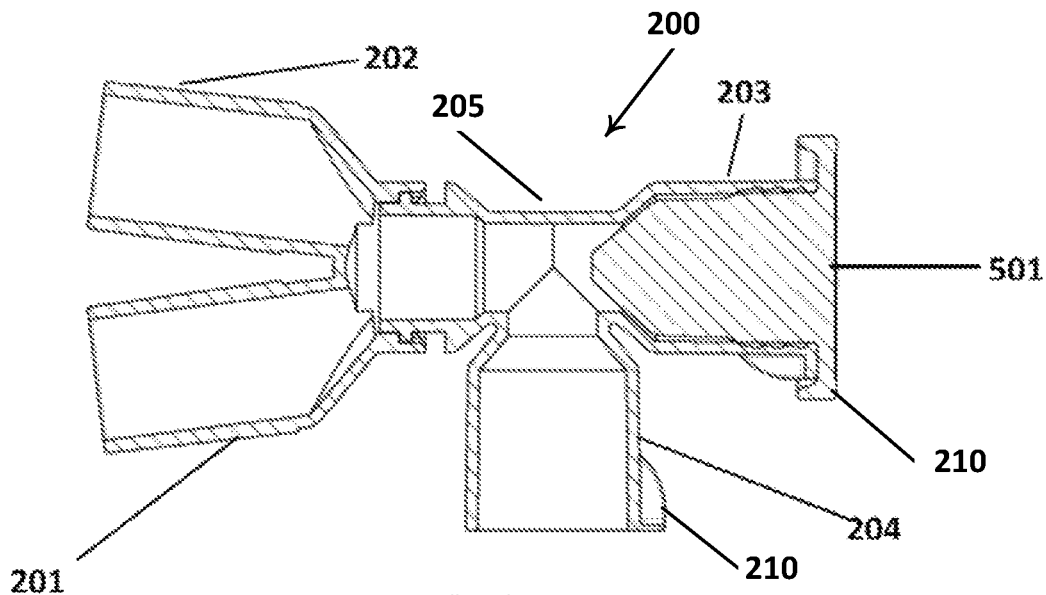

FIGS. 5 and 6 show views similar to those in FIGS. 2 and 4 except that a closure or stopper 501 has been applied to close interface port 204*a*. FIGS. 7 and 8, on the other hand, show the closure or stopper 501 applied to close interface port 203*a*. Thus, when a patient interface is connected to interface port 203*a*, gases may be prevented from flowing through interface port 204*a* per FIGS. 5 and 6 and when a patient interface is connected to interface port 204*a*, gases may be prevented from flowing through interface port 203*a* per FIGS. 7 and 8. This prevention is particularly advantageous for therapies requiring a closed or essentially closed system with a known pressure, flow, or volume of gas such as, but not limited to, e.g., ventilation or assisted breathing arrangements where both inspiratory and expiratory assistance is provided. The stopper may engage the ports 203*a*, 204*a* via a friction or push fit, as shown, although the invention is not limited thereto. As shown in the illustrated embodiments (see, for example, FIG. 6), the closure or stopper 501 may include a flange extending about all or a part of a perimeter thereof, preferably parallel or substantially parallel to the opening formed by the port. This can serve to limit the extent of insertion of the closure or stopper inside the port and further provides leverage in facilitating removal of the closure or stopper from the port. Further as shown, a wall may extend from the flange such that a cavity or recess is formed in which the wall forming the port is received. This may improve the seal. Additionally or alternatively, the port may comprise a flange or rib around an inner or outer surface thereof that is brought into engagement with the stopper or closure when the stopper or closure is fitted to provide for a more secure fit. Further, with appropriate, known constructions, haptic, audible (click), or visual feedback can be generated to indicate to a user that the closure or stopper has been properly fitted.

While the invention is not limited to any particular form of closure, in the embodiment shown in FIGS. 5 to 8, the closure may be conveniently formed, at least in part from a resiliently deformable material, such as an elastomeric material. As will be appreciated, only a portion of the closure may be formed from such a material. For example, only a portion of the closure that engages the inner wall of the interface branch 203, 204 may be resiliently deformable. In FIGS. 5 to 8, the closure 501 includes ribs or ridges 502 which provide for an improved seal while maintaining ease of connecting and disconnecting the closure. Alternatively, the closure may be rigid or substantially rigid. According to such embodiments, a deformable seal may be provided between the engaging surface of the closure 501 and the connector 200. For example, rather than the ribs per FIGS. 5 to 8, one or more O-rings may be provided on a substantially rigid insert.

The closure 501 may be arranged in a suitable shape, e.g. comprising a male projection, for being at least partly received in the cavity formed by a branch to which it is to be connected, in use.

To avoid or reduce an undesired pulling force on the patient interface, the closure 501 may be made of a light weight, e.g. low density material.

Alternatively, or additionally the closure 501 may be provided as a hollow or semi-hollow body thereby minimizing its weight.

It is also advantageous to provide the closure in a shape minimizing the dead space of at least the branch to which it is connected in use. As such the closure 501 may extend into the branch to which it is connected, in use. In some configurations, the closure 501 may comprise a part extending substantially along the entire interior length of the branch and arranged to close the flow path between the main body 205 and said branch, in use. Alternatively, the closure 501 may comprise a part extending at least part-way through the branch, thereby closing off the flow path between the main body 205 and the branch, part-way within the branch.

Alternatively, or additionally, the closure 501 may comprise a tapered or stepped portion for providing a secure or snug fit against the edge or interior peripheral surface of the branch. A tapered or stepped closure 501 may be particularly useful in embodiments where at least two ports, e.g. the first and second interface ports, are of different sizes, since one and the same closure 501 may be used to selectively close either of the associated different sized ports.

While not shown, the closure 501 may include an extension that may be pulled to facilitate removal of the closure 501 from the applicable interface port 203, 204. While the extension may take any form that enables it to be gripped by a user, preferably, the extension is in the form of a loop or hook as this enables the connector 200 to be suspended on a medical stand when not in use. Particularly when the connector 200 is connected to other medical circuit components, this can provide an easy and ordered way of temporarily storing at least parts of a breathing circuit. Additionally or alternatively, the extension may include a flexible arm or loop that is long and flexible enough to enable the closure 501 to be fitted to and removed from one or both of the interface ports while keeping the closure 501 attached to the connector 200, preventing loss and/or dropping.

Additionally or alternatively, the extension may include a hinge, e.g. a living hinge, to enable the closure 501 to be fitted to and removed from one or both of the interface ports while keeping the closure 501 connected to the connector 200.

The connector body 205 may include an integral or attachable circuit hanger in addition to or in lieu of a circuit hanger, such as the hook/loop. The circuit hanger may itself be a hook or loop, or may be a ball configured to mate with a socket on a medical pole or other device to hang the connector, with its optionally connected circuit components, when not in use Also not shown, the closure 501 may have a passage extending therethrough to enable a gases treatment and/or monitoring device to be inserted therethrough. According to such embodiments, a further closure, such as a plug, may be used to close of the passage when a gases treatment or monitoring device is not required, similar to cap 905 shown in FIG. 9.

As shown in FIG. 6, preferably, the closure or stopper 501 extends through the port so as to fill or substantially fill the inside of the relevant interface branch 203, 204. This avoids dead space being formed in the branch not being used to deliver gases to a patient interface by preventing the heated, humidified gases from flowing into an additional portion of the connector, that would otherwise extend the length of the path of gases therethrough and result in further cooling and lead to greater re-breathing of exhaled gas.

Other forms of closure will be apparent to those skilled in the art. For example, threaded caps or valves.

Figure 9:
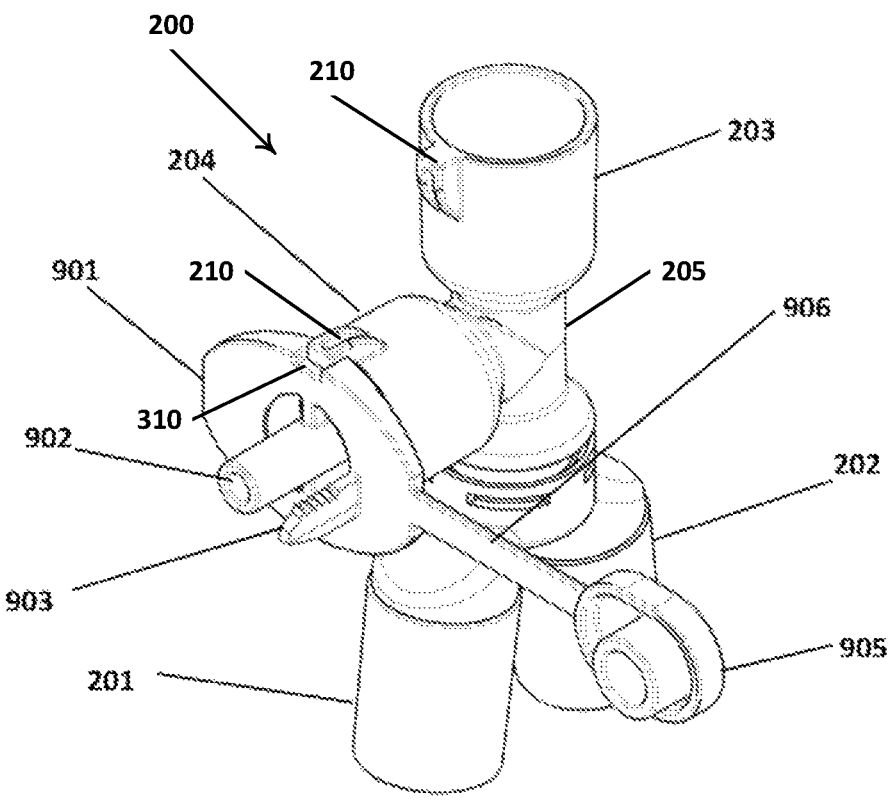
FIGS. 9 to 11 provide perspective, side and sectional views, respectively, of the connector of FIGS. 2 to 4 with a metered dose inhaler connector coupled to an interface port thereof.
Figure 10:
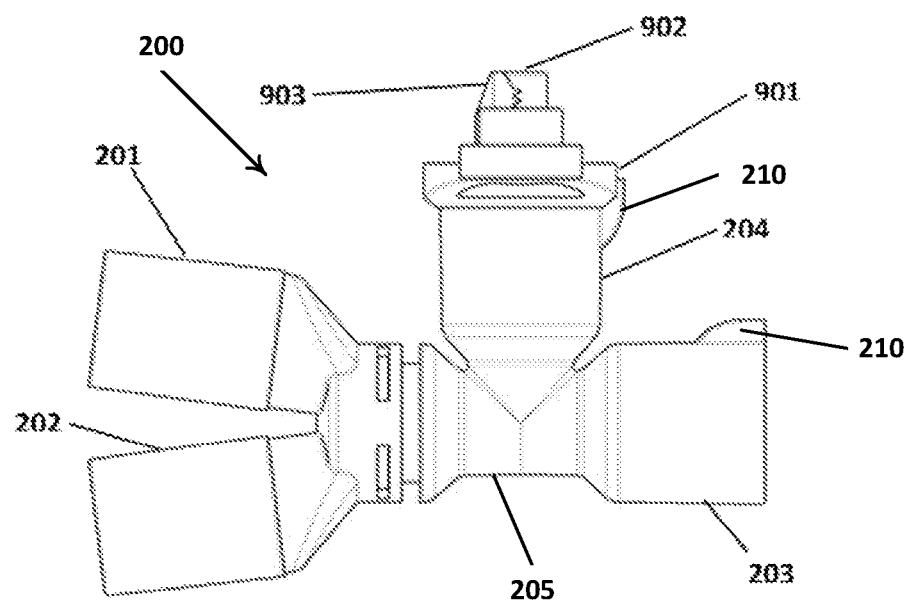
Figure 11:
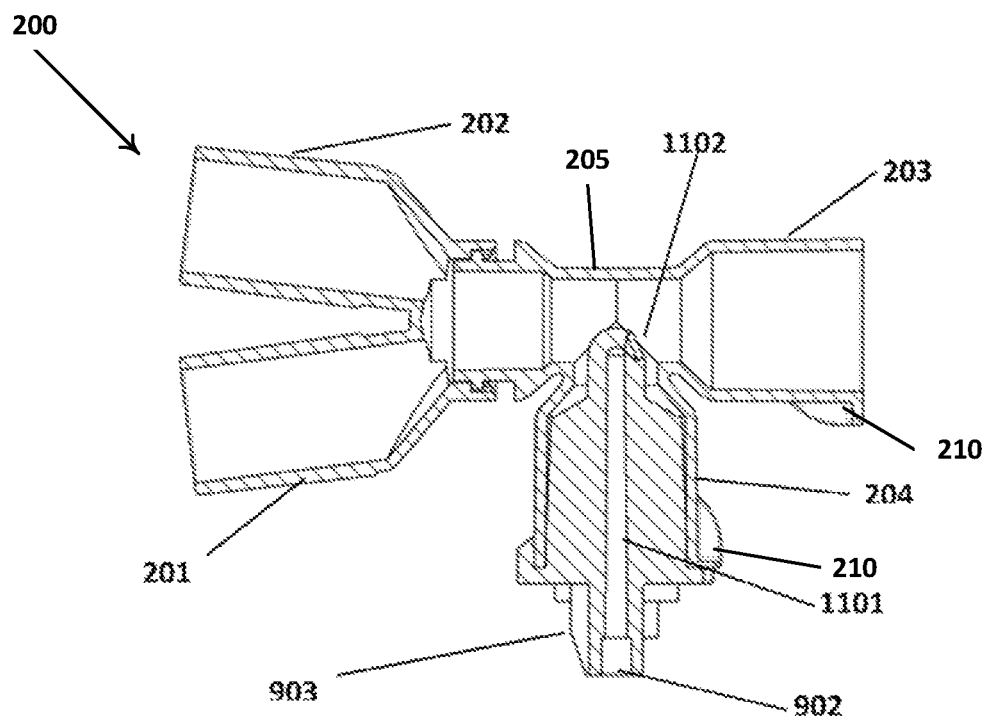
Figure 12:
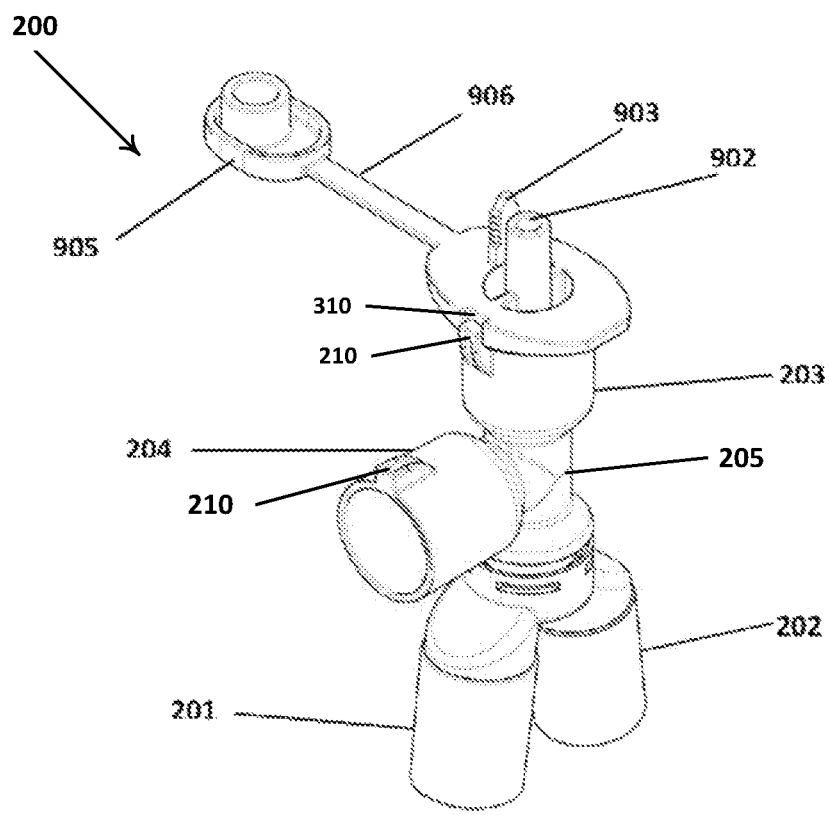
FIGS. 12 to 14 provide perspective, side and sectional views, respectively, of the connector of FIGS. 2 to 4 with a metered dose inhaler connector coupled to another interface port thereof.
Figure 13:
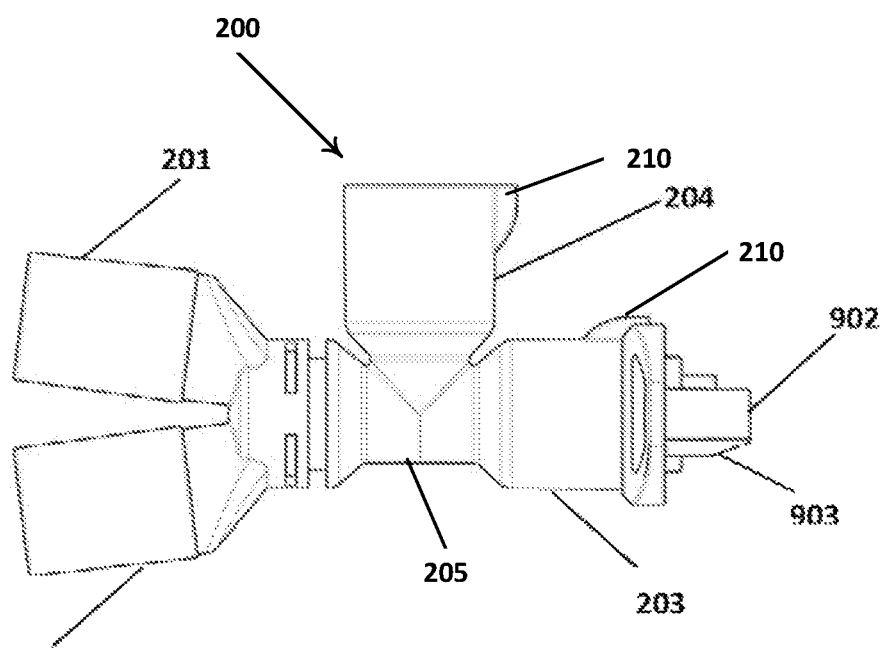
Figure 14:
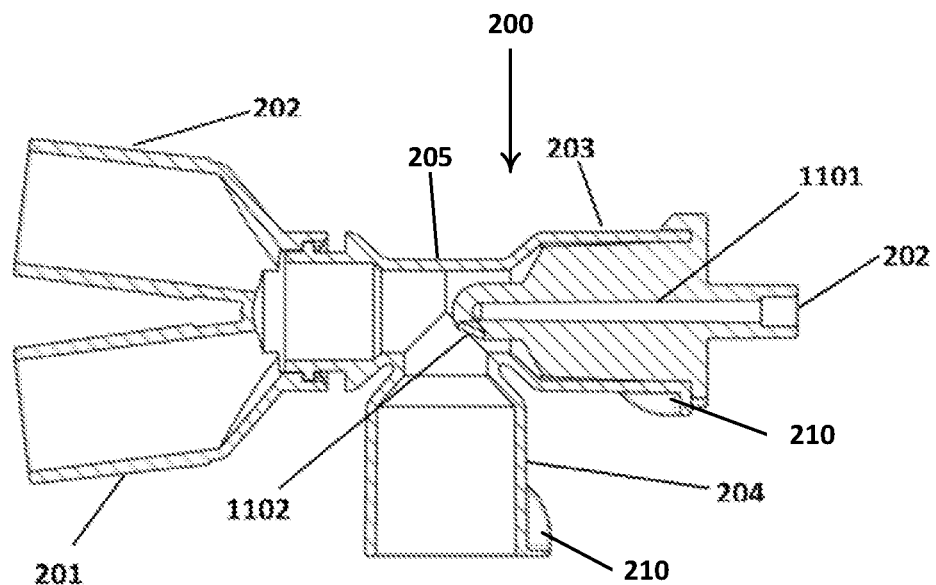
Figure 15:
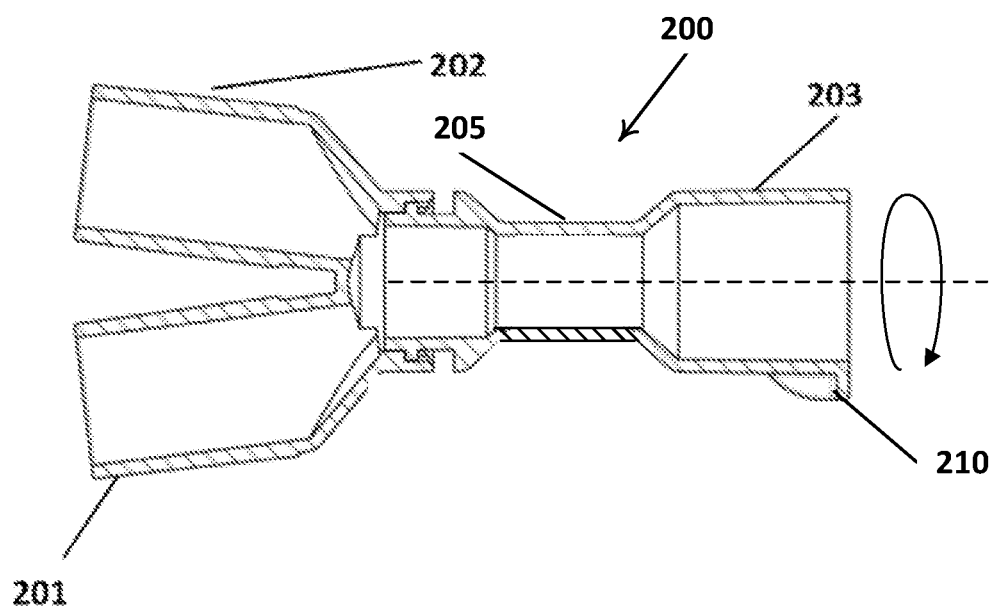
FIGS. 15 to 17 show different connector configurations for a connector comprising a single interface port.
Figure 16:
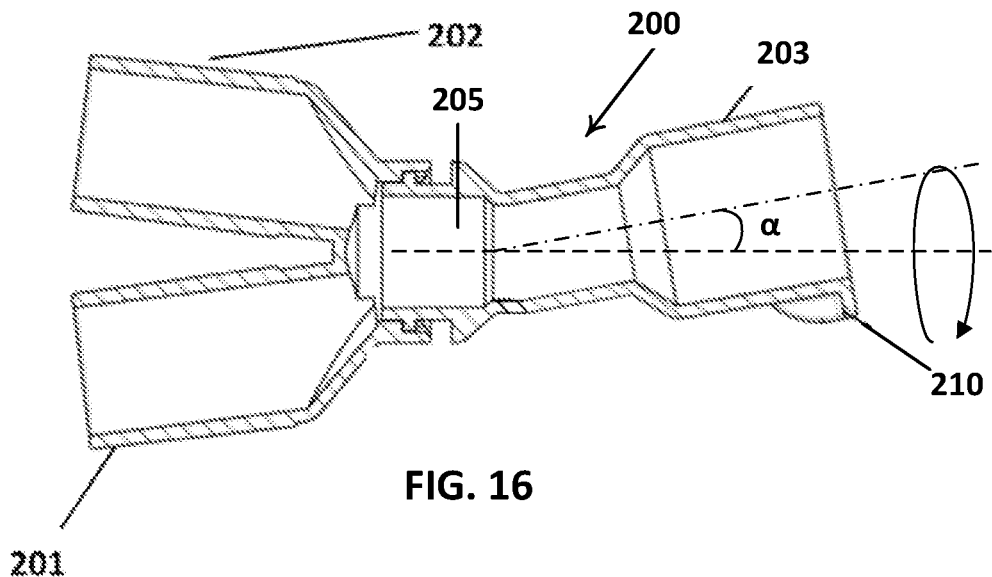
Figure 17:
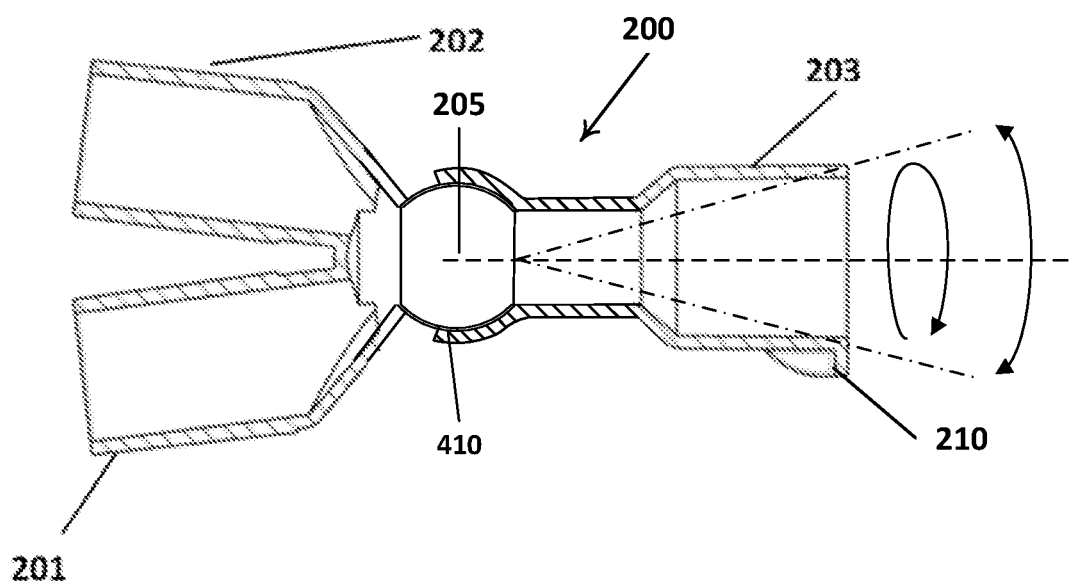

FIGS. 9 to 11 show views similar to those in FIGS. 2 to 4 except that in FIGS. 9 to 11 a metered dose inhaler (MDI) connector 901 is connected to interface port 204a of branch 204. FIGS. 12 to 14, on the other hand, show the MDI connector 901 connected to interface port 203a of branch 203. The MDI connector 901 enables an MDI to be coupled to the connector 200 so that a drug may be administered to a patient in a controlled way. The general design and operation of MDIs and ports and connectors therefor are known. Only points relevant to the present development will be described.

MDIs generally comprise a drug or pharmaceutical reservoir in the form of an aerosol canister. The canister has a short outlet tube extending therefrom, enabling a controlled amount of the drug to be injected into a flow of gases. Once injected, the drug mixes with the gases flowing towards a patient, e.g. within a conduit, for subsequent inhalation by the patient. In order to track usage of the MDI, a counter may be provided. Often this uses a simple mechanical arrangement such as a rack and pinion, whereby when the aerosol canister is urged towards the MDI connector to release the drug, the pinion is caused to rotate by translation of the linear movement of the pinion along the rack into rotation of the pinion, thereby turning a counter. Such arrangements are known.

Thus, as shown in FIGS. 9 to 14, the MDI connector 901 preferably includes a MDI port 902 for sealingly engaging with the outlet tube of an aerosol canister such that drugs released from the canister pass though passageway 1101 to MDI connector outlet 1102 (see FIGS. 11 and 14) and then to the gases flow through the connector 200 for delivery to the patient. As shown, the MDI connector outlet may comprise or be in the form of a diffuser so as to aid in dispersal of the drug over a wider portion of the gases flowing through the connector 200.

As shown, the MDI connector further includes a rack 903 which forms part of a counter for the MDI to monitor usage thereof. Cap 905 may be used to selectively close off MDI port 902 when it is not necessary or desired to administer a drug. The cap 905 may be conveniently mounted on an elongate, flexible arm or loop 906 to prevent it becoming lost or dropped.

Consequently, the interface port 203, 204 of the connector 200 that is not connected to a patient interface may be used to connect to an MDI, avoiding the need for further ports. However, the invention is not limited thereto and one or more auxiliary ports may be provided in the connector 200, including in the branches 201-204 and/or the main body 205. These may be provided for the purposes of connecting to an MDI and/or other gases treatment devices and/or gases monitoring devices.

Further, while the MDI connector 901 of FIGS. 9-14 is shown as being insertable and sealingly engageable with the inner wall of the interface branches 203, 204 similar to the closure 501 shown in FIGS. 5 to 8, the invention is not limited thereto. For example, as shown, the end and/or outer walls of the interface branches 203, 204 may also be engaged. It is also possible that only the outer and/or end walls be engaged with the MDI connector. Further, while the illustrated MDI connector is shown as frictionally or press-fit engaging the connector 200, the invention is not limited thereto. Alternative configurations, similar to those described with respect to closure 501, are also applicable to MDI connector 901.

With reference to FIG. 9, one or more of the branches 201, 202, 203, 204, e.g. one or more of the interface branches 203, 204, and/or the associated ports thereof, may be provided with a first orientation structure 210. The first orientation structure 210 is arranged to align with a corresponding second orientation structure 310 of a unit upon connection of said unit to said branch, in use.

In one configuration the unit may be the closure 501. Additionally or alternatively, the unit may be the MDI connector 901. Additionally or alternatively, the unit may be any other circuit component arranged to be operatively coupled to said branch, e.g. a conduit connector or a patient interface.

In some configurations, such as that shown in FIG. 9, the first orientation structure 210 is arranged to physically contact and receive the corresponding second orientation structure 310, in use.

Additionally or alternatively, the first orientation structure 210 may be arranged to physically guide and receive the corresponding second orientation structure 310 into a mating end position, in use.

The first orientation structure 210 and corresponding second orientation structure 310 may be arranged so as to prevent inadvertent relative rotation between the associated branch and the unit when connected, in use. In this way, a correct rotational orientation between the connected branch and unit may be initiated and then maintained.

In some configurations the MDI connector 901 may comprise directional features. The directional features may indicate or be associated with a general direction of the passageway 1101 of the associated MDI port 902 (see FIG. 11). In some embodiments, the passageway 1101 may extend non-symmetrically through the MDI connector 901. To this end, at least a part of the passageway 1101 may extend at an angle in relation to the sidewalls or main axis of the MDI connector 901. An angled or partially angled passageway 1101 allows for directing the medicament or drug into the gases stream and towards the patient interface when entering the main body 205. In this way the dispensed medicament or drug impinges less on the bulk flow of gas within the main body 205. Moreover, deposition of the medicament against the inner walls of the main body 205 is limited by not directing the medicament or drug directly towards said walls. Also, by directing the medicament or drug towards the patient interface, the risk of the medicament being carried away from the patient by the bias flow of the system is substantially decreased, as it encourages velocity towards the patient, resulting in greater medicament take up and accuracy in the determined dose delivered to a patient. The passageway may comprise a dispenser, such as a nozzle and/or diffuser, that encourages dispersion of the medicament across a volume of the gas, rather than delivering the medicament at a concentrated point.

In some configurations, the directional features may form a passageway through any unit arranged to be connected to at least one of the connector branches 201, 202, 203, 204, e.g. the closure 501 or the MDI connector 901.

In some configurations, directional features may be arranged in connection with an interior wall of the associated connector branch 201, 202, 203, 204. Such directional features may act to direct a medicament or drug dispensed via a medicament delivery port, e.g. a MDI port 902 or a nebulizer port, towards the patient interface, when exiting said medicament delivery port.

In some configurations, the directional features may form an integral part of the associated branch 201, 202, 203, 204.

In some configurations the directional features may form an integral part of at least part of an interior sidewall of the associated branch, thereby creating an at least partly angled flow path through the associated port towards the main body 205.

In some configurations, the directional features are arranged to direct a sensor, or sensing tube connected to one of the branches 201, 202, 203, 204 into a correct position.

In some embodiments, the directional features may comprise an angled surface arranged downstream the downstream end of the medicament passageway 1101, in use. The angled surface being arranged to direct medicaments exiting the medicament passageway 1101 towards the patient interface, thereby forcing the medicaments to change direction after exiting the downstream end of the medicament passageway 1101.

It should be appreciated that any branch and/or associated port of the connector could be provided with any of the different types of aforementioned directional features.

In an embodiment, a circuit kit for a respiratory assistance system is provided. The kit may comprise the aforementioned connector. The kit may further comprise any one or more of: an inspiratory conduit for connection to the inspiratory conduit port of said connector, an expiratory conduit for connection to the expiratory port of the connector, a humidifier chamber, a dry line for operative coupling to a gases source and/or a humidifier chamber, a patient interface, and MDI equipment.

It should be understood that any examples used in this description are in no way limiting, but merely illustrative of possible embodiments for purposes of clarification. Unless the context clearly requires otherwise, throughout this description and the claims that follow, the words "comprise", "comprising", and the like, are to be construed in an inclusive sense as opposed to an exclusive or exhaustive sense, that is to say, in the sense of "including, but not limited to". "Include" and "including" are to be interpreted in the same way.

Reference to any prior art in this description is not, and should not be taken as, an acknowledgement or any form of suggestion that the prior art referenced forms part of the common general knowledge in any relevant field of endeavour in any country in the world.

The present invention may be said broadly to consist in the parts, elements, and features referred to or indicated in this description and the claims that follow, individually or collectively, in any or all combinations of two or more of said parts, elements, or features. Where reference is made to integers or components having known equivalents thereof, those equivalents are herein incorporated as if individually set forth.

It should be noted that various modifications to the embodiments disclosed herein will be apparent to those skilled in the art. Such modifications may be made without departing from the spirit and scope of the present invention and without diminishing its attendant advantages. For instance, various components may be repositioned or reshaped as desired. It is therefore intended that such modifications be included within the scope of the invention. Moreover, not all of the features, aspects, and advantages disclosed herein are necessarily required to practice the present invention. Accordingly, the scope of the present invention is intended to be defined only by the claims that follow.

What is claimed is:

1. A connector for a respiratory assistance system, the connector comprising:
    an inspiratory conduit port,
    an expiratory conduit port,
    a first interface port,
    a second interface port, the first interface port and the second interface port each fluidly couplable to a patient interface,
    a directional feature acting to direct a medicament or drug dispensed via a medicament delivery port or a nebulizer port, at least in part towards the patient interface, when exiting the medicament delivery port or the nebulizer port, the directional feature comprising a passageway asymmetrically provided through one of the inspiratory conduit port, the expiratory conduit port, the first interface port, or the second interface port, the passageway comprising an angled surface arranged proximal a downstream end of the one of the inspiratory conduit port, the expiratory conduit port, the first interface port, or the second interface port, wherein the passageway is provided in a closure configured to selectively close off one of the inspiratory conduit port, the expiratory conduit port, the first interface port, or the second interface port;
    a body or body portion formed between the inspiratory conduit port, the expiratory conduit port and the first and second interface ports, the body or body portion defining an interior cavity that fluidly couples, at least in part, the inspiratory conduit port and the expiratory conduit port to the first and second interface ports,
    wherein the first interface port and the second interface port are rotatably operatively coupled at a joint in relation to the inspiratory conduit port and the expiratory conduit port at least about one axis extending at an angle in relation to a longitudinal axis of either the inspiratory conduit port or the expiratory conduit port so as to change a relative orientation between the first and second interface ports and at least one of the inspiratory conduit port or the expiratory conduit port.

2. The connector of claim 1, wherein the first interface port and the second interface port are rotatably operatively coupled by a swivel or ball joint connection connecting the first interface port and the second interface port to the body or body portion.

3. The connector of claim 1, wherein the angle between the axis around which the first interface port is rotatable and the longitudinal axis of either the inspiratory conduit port or the expiratory conduit port is substantially perpendicular.

4. The connector of claim 1, wherein one or more of said inspiratory conduit port, said expiratory conduit port, said first interface port or said second interface port is operatively couplable to a unit, wherein the one or more of said inspiratory conduit port, said expiratory conduit port, said first interface port or said second interface port comprise a first orientation structure arranged to align with a corresponding second orientation structure of the unit operatively couplable to said one or more of said inspiratory conduit port, said expiratory conduit port, said first interface port or said second interface port, in use.

5. A respiratory assistance system comprising the connector of claim 4, and further comprising the unit, wherein the unit is or comprises:
    the closure,
    one or both of a metered-dose inhaler (MDI) or and MDI connector, or
    a conduit connector.

6. The connector of claim 4, wherein the first orientation structure comprises a recess or projection configured to mate with a corresponding projection or recess of the corresponding second orientation structure.

7. The connector of claim 4, wherein the first orientation structure is arranged to physically guide and receive the corresponding second orientation structure into a mating end position, in use.

8. The connector of claim 4, wherein the first orientation structure and the corresponding second orientation structure are arranged to prevent inadvertent relative rotation between the one or more of said inspiratory conduit port, said expiratory conduit port, said first interface port, or said second interface port and the unit when connected.

9. The connector of claim 1, wherein the passageway is provided through the first interface port or the second interface port.

10. The connector of claim 9, wherein the passageway is asymmetrically arranged within the first interface port or the second interface port.

11. The connector of claim 1, wherein the closure is configured to selectively close off the first interface port or the second interface port.

12. The connector of claim 1, wherein the connector is configured to be coupled with one or more of:
    a metered-dose inhaler,
    a nebulizer, or
    a source of aerosolized medication.

13. The connector of claim 1, wherein the directional feature is arranged in connection with an interior wall of the first interface port or the second interface port.

14. The connector of claim 1, wherein the directional feature is configured to one or more of:
    form an integral part of one of said port, said expiratory conduit port, said first interface port, or said second interface port, form an integral part of at least part of an interior sidewall of said inspiratory conduit port, said expiratory conduit port, said first interface port, or said second interface port, or direct a sensor, or a sensing tube connected to one of said inspiratory conduit port, said expiratory conduit port, said first interface port, or said second interface port, into a correct position or orientation.

15. A circuit kit for a respiratory assistance system, comprising,
 a connector according to claim 1, and any one or more of:
   an inspiratory conduit for connection to the inspiratory conduit port of said connector,
   an expiratory conduit for connection to the expiratory port of the connector,
   a humidifier chamber,
   a dry line for operative coupling to one or both of a gases source or a humidifier chamber,
   the patient interface, or
   MDI equipment.

16. The connector of claim 1, wherein an orientation of the first interface port is alterable between at least two configurations in relation to the inspiratory and expiratory conduit ports, said at least two configurations comprising:

a first configuration in which the inspiratory and expiratory conduit ports are adjacent one another at a first end of the connector and the first interface port is at a second end of the connector generally opposite the first end, the first interface port and the inspiratory and expiratory conduit ports being arranged such that flow through each of the inspiratory and expiratory conduit ports is substantially parallel, and a second configuration in which the first interface port is at an angle in relation to a longitudinal axis of the body or body portion, wherein the connector is releasably lockable in at least the first and/or second configurations.

* * * * *